United States Patent [19]
Rinehart et al.

[11] Patent Number: 5,952,332
[45] Date of Patent: Sep. 14, 1999

[54] ANTIVIRAL AND CYTOTOXIC COMPOUNDS FROM THE SPONGE CRAMBE CRAMBE

[75] Inventors: Kenneth L. Rinehart; Elizabeth A. Jares-Erijman, both of Urbana, Ill.

[73] Assignee: Pharma Mar, s.a., Madrid, Spain

[21] Appl. No.: 09/040,580

[22] Filed: Mar. 18, 1998

Related U.S. Application Data

[63] Continuation of application No. 08/476,871, Jun. 7, 1995, Pat. No. 5,756,734, which is a continuation of application No. 07/944,152, Sep. 11, 1992, abandoned.

[51] Int. Cl.⁶ ........................ A61K 31/505; C07D 491/20
[52] U.S. Cl. ............................................ 514/258; 544/231
[58] Field of Search ............................... 544/231; 514/258

[56] References Cited

PUBLICATIONS

Schmitz et al., *Journal of Natural Products,* vol. 54, No. 6, pp. 1469–1490 (1991).
Kashman et al., *J. Amer. Chem. Soc.,* 111: 8925–8926 (1989).
Rosano et al., *J. Backeriol.,* 135: 805–808 (1978).
Harbour et al.,*J. Amer. Chem. Soc.,* 103: 5604–5606 (1981).
Berlinck et al., Tetrahedron Letters, 31: 6531–6534 (1990).
Jares–Erijman et al.,*J. Organic Chemistry,* vol. 56, No. 19, 5712–5715 (1991).

*Primary Examiner*—Emily Bernhardt
*Attorney, Agent, or Firm*—Ernest V. Linek; Banner & Witcoff, Ltd.

[57] ABSTRACT

The present invention is directed to several novel compounds isolated from the sponge *Crambe crambe*, and designated herein as Crambescidin 816 (Compound 1), Crambescidin 830 (Compound 2), Crambescidin 844 (Compound 3), and Crambescidin 800 (Compound 4), as well as several derivatives thereof. The 816, 830, 844 and 800 compounds are four preferred species of complex pentacyclic guanidines linked by a linear ω-hydroxy fatty acid to a hydroxyspermidine, that have been obtained by a bioassay-guided isolation procedure, involving solvent partition and chromatography on Sephadex LH-20, cyano, and C-18 columns, from extracts of the red, encrusting sponge *Crambe crambe* (Order Poecilosclerida, Family Esperiopsidae).

3 Claims, 11 Drawing Sheets

ANTIVIRAL AND CYTOTOXIC COMPOUNDS FROM THE SPONGE CRAMBE CRAMBE

CROSS-REFERENCE TO RELATED APPLICATION

The present invention is a continuation of application Ser. No. 08/476,871, Jun. 7, 1995, now U.S. Pat. No. 5,756,734 which is a continuation of Ser. No. 07/944,152, filed Sep. 11, 1992, now abandoned.

SUMMARY OF THE INVENTION

The present invention is directed to several novel compounds isolated from the sponge *Crambe crambe*, and designated herein as Crambescidin 816 (Compound 1), Crambescidin 830 (Compound 2), Crambescidin 844 (Compound 3), and Crambescidin 800 (Compound 4), as well as several derivatives thereof. The 816, 830, 844 and 800 compounds are four preferred species of complex pentacyclic guanidines linked by a linear ω-hydroxy fatty acid to a hydroxyspermidine, that have been obtained by a bioassay-guided isolation procedure, involving solvent partition and chromatography on Sephadex LH-20, cyano, and C-18 columns, from extracts of the red, encrusting sponge *Crambe crambe* (Order Poecilosclerida, Family Esperiopsidae).

In assays on board the R/V Garcia del Cid during a 1988 Pharma Mar S.A. expedition to the Western Mediterranean, extracts of *C. crambe* were regularly active in vitro against Herpes simplex virus, type 1 (HSV-1), and cytocoxic to L1210 murine leukemia cells. Compounds 1, 3, and 4 inhibit HSV-1 completely in vitro, with diffuse cytotoxicity, at 1.25 μg/well and are 98% effective against L1210 cell growth in vitro at 0.1 μg/mL. It is believed that such activity will extend to in vivo uses of these compounds as well.

The Crambescidins' pentacyclic guanidine moiety has been isolated only once before (see, Kashman et al., *J. Amer. Chem. Soc.*, 111: 8925–8926 (1989)) and a hydroxyspermidine unit from a marine source is unprecedented. For instance, there is only one known report of a hydroxyspermidine moiety from a natural source (bacterial); see, Rosano et al., *J. Bacteriol.*, 135: 805–808 (1978).

SCHEME I

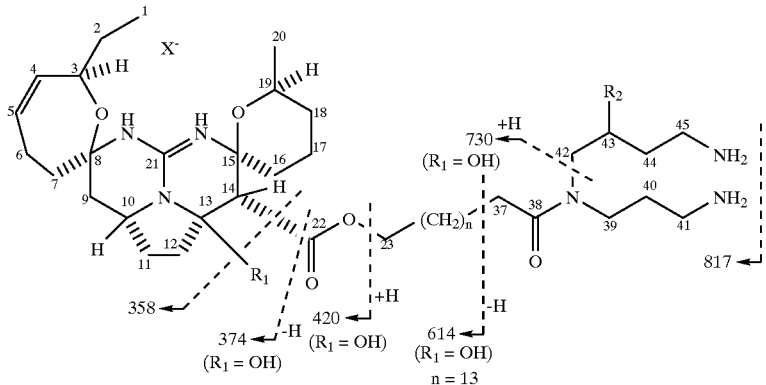

1: $R_1 = R_2 = OH, n = 13$
2: $R_1 = R_2 = OH, n = 14$
3: $R_1 = R_2 = OH, n = 15$
4: $R_1 = H, R_2 = OH, n = 13$
5: $R_1 = R_2 = H, n = 13$

SCHEME II

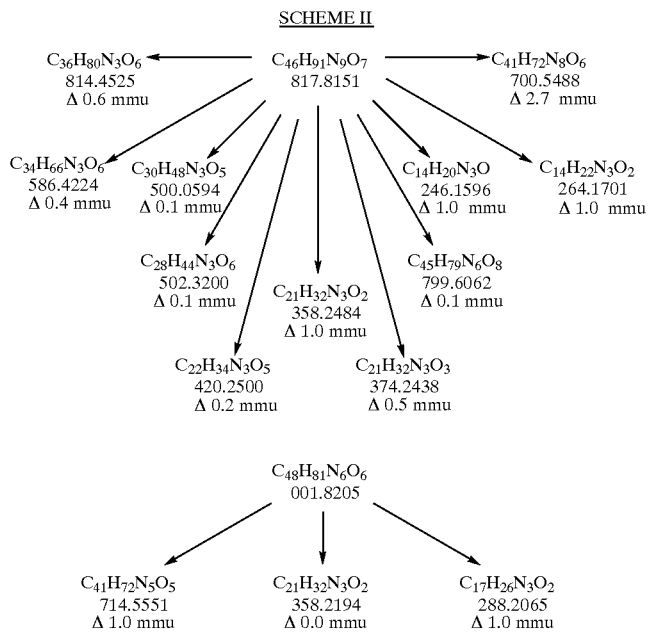

BRIEF DESCRIPTION OF THE DRAWINGS

FIGS. 4b and 4c show details of the HMBC (MeOD) spectrum shown in FIG. 4a.

FIG. 6b is an overlaid plot of 45-COSY and 45-RELAY COSY spectra of Crambescidin 816.

FIG. 7-1 and 7-2 shows the FA-MS spectra of the Crambescidins, 816 (Compound 1), 800 (Compound 4), 830 (Compound 2) and 844 (Compound 3).

DETAILED DESCRIPTION OF THE INVENTION

Figure 1:
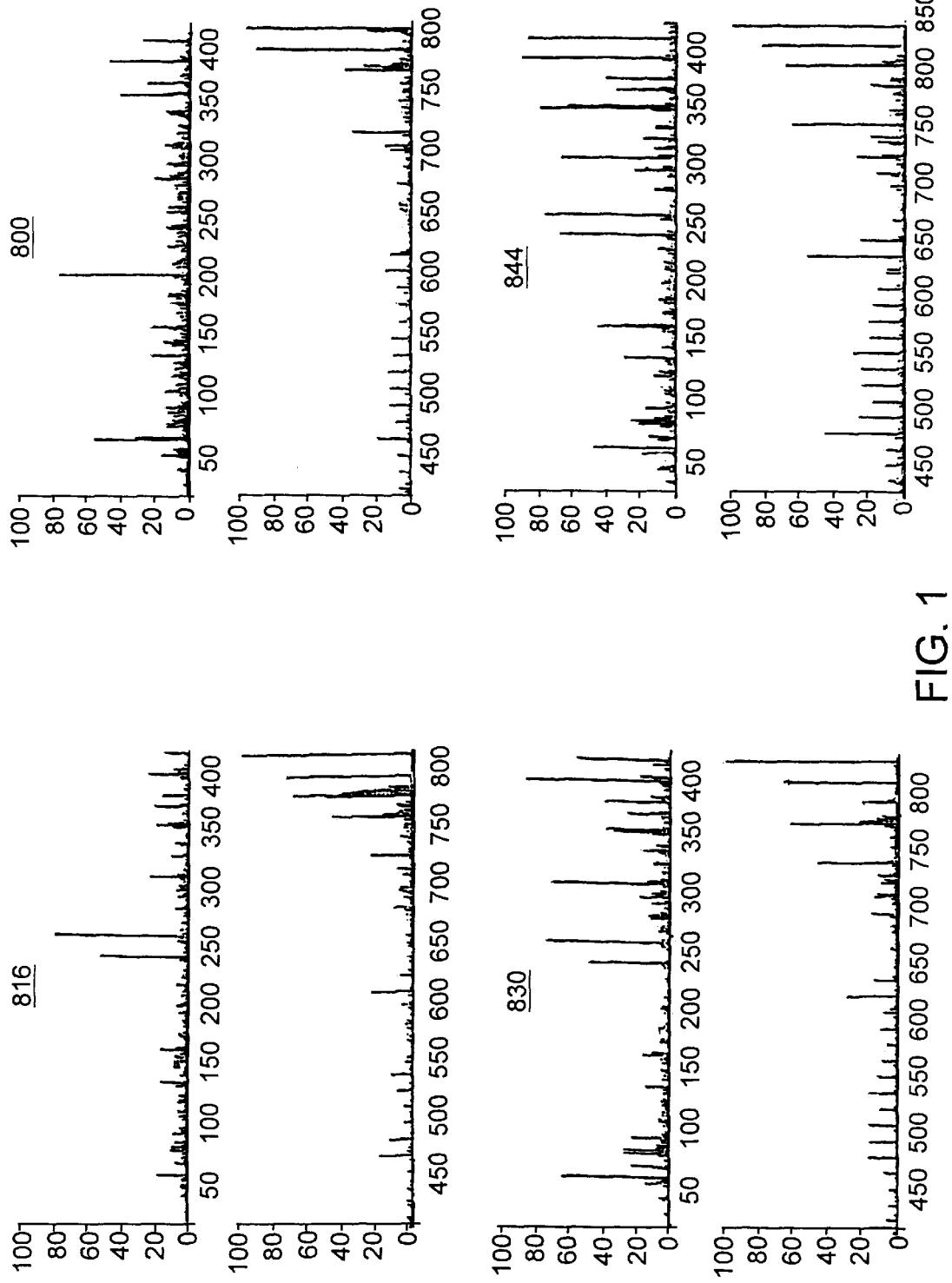
FIG. 1 shows the FABMS/MS spectra of the Crambescidins, 816 (Compound 1), 800 (Compound 4), 830 (Compound 2) and 844 (Compound 3).

Crambescidin 816 (Compound 1), the most abundant component isolated to date, was assigned the molecular formula $C_{45}H_{80}N_6O_7$ by HRFABMS (M+H 817.6151, Δ1.6 mmu), indicating 9 degrees of unsaturation. The hydroxyspermidine region of Compound 1 was assigned first. HRFABMS data on fragmentation ions at m/z 730 (M+H−87) and 614 (M+H−203, Schemes I and II), which are derived (tandem FAB, FABMS/MS, Scheme II) from the M+H ion (m/z 817), indicated losses of $C_4H_9NO$ and $C_9H_{21}N_3O_2$, respectively.

The numbering of carbons follows that previously employed for ptilomycalin A (Compound 5) and is strictly valid for Compounds 1, 4, 10 and 5. For Crambescidin 830 (Compound 2) one extra carbon (a CH$_2$ group) is added (arbitrarily C-30a) and for Crambescidin 844 (Compound 3), two extra (again, CH$_2$ groups, arbitrarily C-30a and C-30b).

The $C_4H_9NO$ unit was assigned, from $^1$H COSY and Relay COSY data, as subunit a and extended to subunit b (giving the $C_9H_{21}N_3O_2$ loss) by COLOC correlations between C-38 (δ 177.5) and both H-42a and H-37, as well as by COSY spectra showing connectivities between H-39a, H-39b, and H-40 and between H-40 and H-41 ($^1$H NMR data in Table I). $^{13}$C NMR assignments (Table II) for the 3-hydroxyspermidine unit based on CSCM data were in agreement with values calculated from the chemical shifts of the spermidine residue of ptilomycalin A (Compound 5). A polymethylene chain (suggested by $^1$H NMR) from C-37 to -23 was assigned by FABMS data, which provided a nearly unbroken series of homologous fragment ions from cleavages at successive methylene groups from m/z 614.4525 ($C_{36}H_{60}N_3O_5$ Δ0.8 mmu) to m/z 420.2500 ($C_{22}N_3O_5$ Δ0.2 mmu), extending b to subunit c.

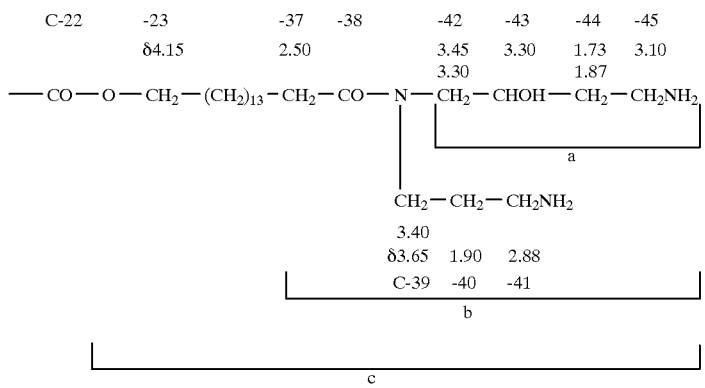

The mass spectral data (Schemes I and II) demonstrate an additional loss of $CO_2$ with hydrogen transfer from 420.2500 to give m/z 374.2438 ($C_{21}H_{32}N_3O_3\Delta 0.5$ mmu). This second carboxyl carbon at δ 168.7 and two doubly deshielded quaternary carbons (N,O-disubstituted from the chemical shifts) at δ 90.5 (C-13) and δ 84.5 are correlated (long-range C—H, COLOC) with a singlet proton at δ 3.46, establishing subunit d. Moreover, subunit d abuts subunit c, since C-22 (δ168.7) can be correlated by HMBC wish H-23 (δ 4.15).

Three isolated spin systems e–g identified from COSY and CSC, data were connected by long-range C—H correlations observed in COLOC and HMBC spectra. A terminal hydrogen (H-7b) in subunit e and H-9b in subunit f both correlated with a doubly deshielded quaternary carbon (C-8, N,O-disubstituted) at δ 85.1, and another terminal hydrogen (H-12b) in subunit f correlated with the quaternary carbon (C-13) at δ 90.5. The remaining quaternary carbon (C-15) at δ 84.5 correlated to the protons on C-16 (HMBC). Thus, these units could be combined as subunit h, where the oxygens other than the carboxyl must be present in two cyclic ethers and a hydroxyl group. The latter is located on C-13 as shown by the difference in chemical shift of C-13 in 4, which lacks the hydroxyl. Therefore, the cyclic ethers join C-3, -8, -15 and -19.

A signal at δ 147.9 (149.5 in $CD_3OD$) in the $^{13}C$ NMR spectrum of 1 with no companion olefinic carbon indicates a tetrasubstituted guanidine group (in salt form), providing the nitrogens on C-8, -10, -13, and -15. Moreover, in the $^1H$ NMR ($CDCl_3$) spectrum the $D_2O$-exchangeable signal appearing at δ 10.01 on irradiation shows NOE of H-3 and the $D_2O$-exchangeable signal at δ 10.03 shows NOE of H-19 (Scheme III), arguing that (i) the guanidine nitrogens on C-8 and -15 (ether bearing) are monosubstituted (and the N-10 (=N-13) nitrogen disubstituted) and (ii) O-3 is attached to C-8 and O-19 to C-15, or vice versa. The guanidine would then for geometric reasons exist in a rigid 6-5-6 ring system with C-3 to C-8 and C-15 to C-19 in 7- and 6-membered cyclic ether bridges, respectively (the reverse C-3 to C-15 and C-8 to C-19 in 14- and 13-membered either bridges being essentially impossible on geometric grounds). The nature of the counterion was not determined but, because several isolation steps involved contact with NaCl, this was presumably $Cl^-$.

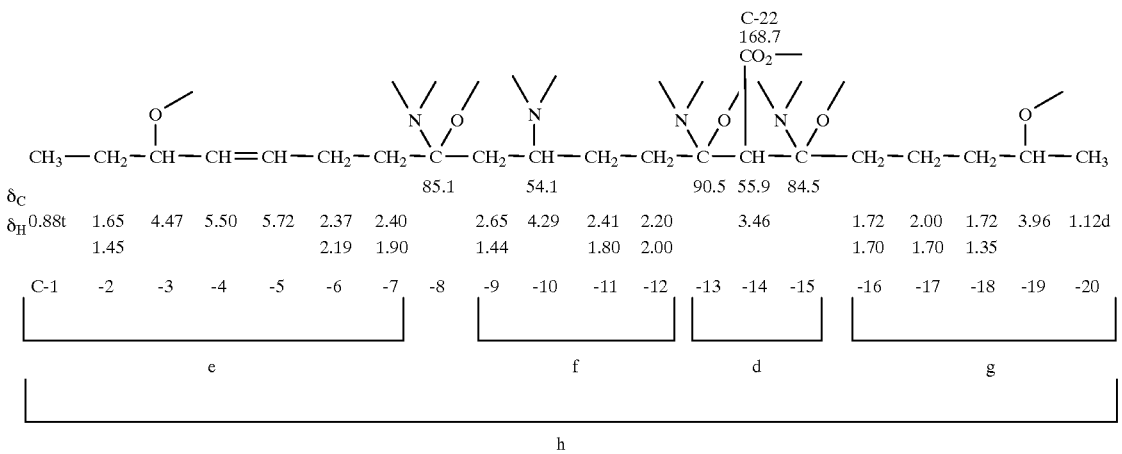

SCHEME III

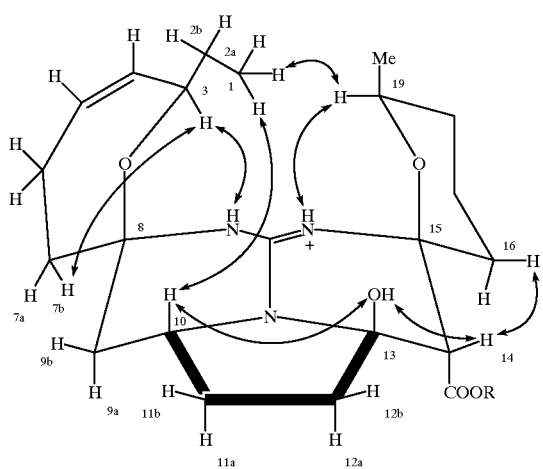

Comparison of the $^1$H and $^{13}$C NMR data reported for ptilomycalin (Compound 5×see, Berlinck et al., supra) with those for Compound I (Tables I and II) argue the presence of the same ring system and, probably, the same relative stereochemistry.

TABLE I $^1$H NMR Data for Crambescidin 816 (1, MeOD)

| | δ, mult (J in Hz) | | δ, mult (J in Hz) |
|---|---|---|---|
| H-1 | 0.88, t (7.0) | H-17a | 1.70, m |
| H-2a | 1.45, ddq (15.5, 10.0, 7.0) | H-17b | 2.00, m |
| H-2b | 1.65, m | H-18a | 1.35, m |
| H-3 | 4.47, br d (10.0) | H-18b | 1.72, m |
| H-4 | 5.50, br d (11.0) | H-19 | 3.96, m |
| H-5 | 5.72, br t | H-20 | 1.12, d (6.5) |
| H-6a | 2.19, m | H-23 | 4.15, t (6.5) |
| H-6b | 2.37, m | H-24 | 1.62, m |
| H-7a | 1.95, m | H-37 | 2.50, m |
| H-7b | 2.40, m | H-39a | 3.40, m |
| H-9a | 1.44, t (13.0) | H-39b | 3.65, m |
| H-9b | 2.65, dd (13.0, 4.5) | H-40 | 1.90, m |
| H-10 | 4.29, m | H-41 | 2.88, m |
| H-11a | 1.60, m | H-42a | 3.30, m |
| H-11b | 2.41, m | H-42b | 3.45, m |
| H-12a | 2.00, m | H-43 | 3.96, m |
| H-12b | 2.20, m | H-44a | 1.73, m |
| H-14 | 3.46, s | H-44b | 1.87, m |
| H-16a | 1.65, m | H-45 | 3.10, m |
| H-16b | 1.87, m | | |

TABLE II $^{13}$C NMR Data for Crambescidins 816 (1), 800 (4) and 844 (3), and Ptilomycalin A (5)

| | δ (ppm), m$^a$ crambescidin 816 (1) | | δ (ppm), m$^{a,b}$ crambescidin 800 (4) | δ (ppm), m$^a$ ptilomycalin A (5) | δ (ppm), m$^{a,c}$ crambescidin 844 (3) |
|---|---|---|---|---|---|
| | MeOD | CDCl$_3$ | MeOD | CDCl$_3$ | MeOD |
| C-1 | 10.9, q | 10.1, q | 9.4, q | 10.21 | 10.9, q |
| C-2 | 26.4, t | 29.0, t | 26.2, t | 29.19 | 26.5, t |
| C-3 | 72.5, d | 71.2, d | 72.2, d | 70.89 | 72.5, d |
| C-4 | 134.3, d | 133.6, d | 133.0, d | 133.69 | 134.3, d |
| C-5 | 131.3, d | 129.7, d | 129.3, d | 129.96 | 131.3, d |
| C-6 | 24.4, t | 25.8, t | 23.0, t | 23.74 | 24.4, t |

TABLE II-continued $^{13}$C NMR Data for Crambescidins 816 (1), 800 (4) and 844 (3), and Ptilomycalin A (5)

| | δ (ppm), m$^a$ crambescidin 816 (1) | | δ (ppm), m$^{a,b}$ crambescidin 800 (4) | δ (ppm), m$^a$ ptilomycalin A (5) | δ (ppm), m$^{a,c}$ crambescidin 844 (3) |
|---|---|---|---|---|---|
| | MeOD | CDCl$_3$ | MeOD | CDCl$_3$ | MeOD |
| C-7 | 38.2, t | 36.8, t | 36.5, t | 36.22 | 38.2, t |
| C-8 | 85.1, s | 83.5, s | 83.6, s | 86.86 | 85.1, s |
| C-9 | 37.5, t | 36.8, t | 37.1, t | 36.89 | 37.5, t |
| C-10 | 54.1, d | 52.4, d | 54.1, d | 54.06 | 54.1, d |
| C-11 | 30.0, t | 29.7, t | 30.2, t | 30.65 | 30.8, t |
| C-12 | 37.7, t | 36.8, t | 28.2, t | 26.81 | 37.7, t |
| C-13 | 90.5, s | 88.6, s | 52.5, d | 52.13 | 90.5, s |
| C-14 | 55.9, d | 54.4, d | 49.4, d | 50.10 | 55.9, d |
| C-15 | 85.4, s | 83.0, s | 80.6, s | 80.82 | 84.5, s |
| C-16 | 32.8, t | 41.5, t | 32.8, t* | 31.68 | 32.5, t |
| C-17 | 19.1, t | 18.0, t | 18.1, t | 18.01 | 19.1, t |
| C-18 | 32.4, t | 32.0, t | 32.1, t* | 32.06 | 32.9, t |
| C-19 | 70.0, d | 68.7, d | 70.9, d | 67.12 | 70.0, d |
| C-20 | 21.7, q | 21.4, q | 20.4, q | 21.56 | 21.7, q |
| C-21 | 149.5, s | 148.0, s | 151.3, s | 149.09 | 149.6, s |
| C-22 | 168.7, s | 167.1, s | 168.6, s | 168.58 | 168.8, s |
| C-23 | 67.1, t | 65.9, t | 65.1, t | 65.53 | 67.0, t |
| C-24 | 29.6, t | 28.3, t | 29.3, t | 28.54 | 30.3, t |
| C-36 | 27.0, t | 25.7, t | 25.6, t | 25.74 | 26.7, t |
| C-37 | 34.2, t | 32.0, t | 32.8, t* | 33.21 | 39.2, t |
| C-38 | 177.5, s | 175.4, s | 176.0, s | 174.87 | 177.5, s |
| C-39 | 43.9, t | 44.1, t | 42.5, t | 42.13 | 43.9, t |
| C-40 | 26.6, t | 25.8, t | 25.3, t | 27.03 | 26.6, t |
| C-41 | 38.3, t | 36.9, t | 36.5, t | 36.13 | 38.2, t |
| C-42 | 54.8, t | 54.4, t | 53.4, t | 47.59 | 54.8, t |
| C-43 | 68.5, d | 65.9, d | 67.0, d | 26.07 | 68.5, d |
| C-44 | 32.9, t | 31.9, t | 32.3, t | 26.43 | 33.0, t |
| C-45 | 38.5, t | 37.1, t | 37.1, t | 39.25 | 38.5, t |

$^a$Multiplicities were determined by DEPT spectra: q, methyl; t, methylene; d, methine; s, quaternary carbons.
$^b$Signals marked * may be interchanged.
$^c$See ref 4 regarding numbering.

TABLE III

Experimental and Calculated$^a$ $^{13}$C NMR Values For The Hydroxyspermidine Unit of Crambescidin 816

| | Experimental (ppm) | Calculated (ppm) |
|---|---|---|
| C-39 | 43.8 | 42.1 |
| C-40 | 26.6 | 27.0 |
| C-41 | 38.3 | 39.5 |
| C-42 | 54.7 | 55.2 |
| C-43 | 68.5 | 65.1 |
| C-44 | 32.9 | 34.0 |
| C-45 | 38.5 | 38.4 |

$^a$Pretsch, E., et al., Tables of Spectral Data for Structure Determination of Organic Compounds, 2nd Ed., Springer-Verlag, Berlin, 1988.

TABLE IV

NOE Difference Results

| | Irradiated proton | NOE correlation |
|---|---|---|
| CD$_3$OD | H-5 | H-4, H-6a |
| | H-4 | H-5, H-3, H-2a, H-2b |
| | H-3 | H-4, H-7b, H-1 |
| | H-10 | H-9b, H-11b, H-1 |
| | H-14 | H-16b |
| | H-9b | H-9a, H-10 |
| | H-9a + 2a | H-2b, H-3, H-4, H-1, H-9b, H-11a |

TABLE IV-continued

NOE Difference Results

| | Irradiated proton | NOE correlation |
|---|---|---|
| CDCl$_3$ | H-1 | H-2a, H-2b, H-3, H-19 |
| | NH (10.01 ppm) | H-3 |
| | NH (10.04 ppm) | H-19 |
| | H-3 | NH (10.01 ppm) |
| | OH-13 | H-14, H-10 |

The relative stereochemistry of Compound 1 was assigned by NOE difference spectra (CD$_3$OD and CDCl$_3$) and ROESY (CDCl$_3$). An NOE between OH-13 (δ 5.82, CDCl$_3$) and H-14 (δ 3.38, CDCl$_3$) as well as H-10 (δ 4.32, CDCl$_3$) in the ROESY and NOE difference spectra in CDCl$_3$ located them all on the same side of the molecule, and an NOE observed between H-10 and H-9b (δ 2.58, CDCl$_3$), together with the observed coupling constants between H-10 and H-9a (J=13 Hz) and H-9b (J=4.5 Hz), confirmed the relative stereochemistry at C-10. The NOE between H-1 and H-10 assigned the relative stereochemistry at C-8, while an NOE between H-3 (δ 4.55, CDCl$_3$) and the guanidine NH at 610.01 (cf. above) assigned the relative stereochemistry at C-3. Similarly, NOE's between the guanidine NH at δ 10.03 and H-19 and between H-19 and H-1 assigned the relative stereochemistry at C-15 and C-19 (Scheme III).

Crambescidin 830 (Compound 2) (HRFABIIS, 831.6300, M+H; Δ2.3 mmu for C$_{46}$H$_{83}$N$_6$O$_7$) differs from 1 by a CH$_2$ group. FABMS/MS of m/z 831 gave fragments at m/z 744 (M+H−87) and 628 (M+H−203), differing from the corresponding MS/MS peaks for Compound 1 by 14 mu, but the fragments 420, 374, and 358 were the same as in the spectrum of Compound 1, indicating that Compound 2 has the additional CH$_2$ in the polymethylene chain.

Similarly, Crambescidin 844 (Compound 3) differs from Compound 1 by two methylene groups in the polyethylene chain (FABMS/MS).

Crambescidin 800 (Compound 4) (HRMS, 801.6205, M+H; Δ1.3 mmu for C$_{45}$H$_{81}$N$_6$O$_6$) differs from Compound 1 by an oxygen (hydroxyl group). FABMS/MS of m/z 801 shows fragments corresponding to M+H−87 and M+H−203, identifying the hydroxyspermidine unit. At the same time, the presence of m/z 358 (Δ0.0 mmu for C$_2$H$_{32}$N$_3$O$_2$) and 404 and the absence of m/z 374 and 420 indicate that there is a missing oxygen atom at C-13 in the pentacyclic guanidine portion, as confirmed by the doublet (J=5.6 Hz) for H-14 replacing the singlet observed for the same proton in Compound 1.

Compounds 1–4 are probably biosynthetically related to crambines A and B, bioinactive guanidine derivatives that were recently isolated from the same sponge (see, Berlinck et al., *Tetrahedron Letters*, 31: 6531–6534 (1990)), and to ptilocaulin and isoptilocaulin as well (see, Harbour et al., *J. Amer. Chem. Soc.*, 103: 5604–5606 (1981)).

The present invention will be further illustrated with reference to the following examples which aid in the understanding of the present invention, but which are not to be construed as limitations thereof. All percentages reported herein, unless other-wise specified, are percent by weight. All temperatures are expressed in degrees Celsius.

EXAMPLES

General—NMR spectra were obtained with QE-300 (300 MHz, $^1$H; 75 MHz $^{13}$C); NT-360 (360 MHz, $^1$H), or GN-500 (500 MHz, $^1$H; 125 MHz, $^{13}$C) spectrometers; chemical shifts (δ) are reported in ppm referenced to the solvent peak. High- and low-resolution fast-atom bombardment (FAB) mass spectra were measured on a ZAB-SE spectrometer, FABMS/MS spectra on a 70 SE-4F instrument in the Mass Spectrometry Laboratory, School of Chemical Sciences, University of Illinois, Urbana, Ill. HPLC was performed on a system equipped with a Model 110A pump and a Model R-401 differential refractometer, using either a cyano column (25 cm, 0.5 cm i.d., 10-μm particle size, CH$_3$CN:0.01 M NaCl=9:1) or a C-18 column (25 cm, 0.8 cm i.d., 5-μm particle size, MeOH:0.1 M NaCl=9:1).

Example 1
Extraction and Isolation

Isolation of Compounds 1–4 was guided by performing HSV-1 antiviral assays on all extracts and separated fractions. *C. crambe* sponges (sample 12-10-88-2-14) were collected by SCUBA (0 to 9 m) in October 1988 from Isla de Formentor (cueva), Palma de Mallorca, Spain (39°55'05"N/3°08'05"E) and were identified by Dr. M. J. Uriz-Lespe, Pharma Mar S. A. The material was kept frozen until extracted with MeOH-toluene (3:1).

The extract was evaporated in vacuo to give 4.65 g, which was partitioned between CHCl$_3$ and 1 M NaCl (1:1, 100 mL×3). Separation of the chloroform-soluble (bioactive) fraction on LH-20 with MeOH afforded a bioactive fraction (1.97 g), which was partitioned with hexane-EtOAc-MeOH-H$_2$O (4:7:4:3). The active lower phase (1.4 g) was purified by HPLC (cyano column, flow rate 1.8 mL/min.), affording four fractions. Separation of the active fraction (t$_r$=9.8 min.) on a reversed-phase (C-18) column (flow rate, 1.8 mL/min.) afforded the Crambescidins 800 (Compound 2, t$_r$ 8.30 min. 9 mg, 0.2% dry weight), 816 (Compound 1, t$_r$ 8.75 min., 50 mg, 1.1%), and 830 (Compound 3, t$_r$ 10 min., 3.5 mg, 0.1%) and a fraction which was further purified by HPLC with the same C-18 column and solvent at a flow rate of 1.2 mL/min. to give Crambescidin 844 (Compound 4, t$_r$ 15.2 min.).

Crambescidin 816 (Compound 1)

Figure 2:
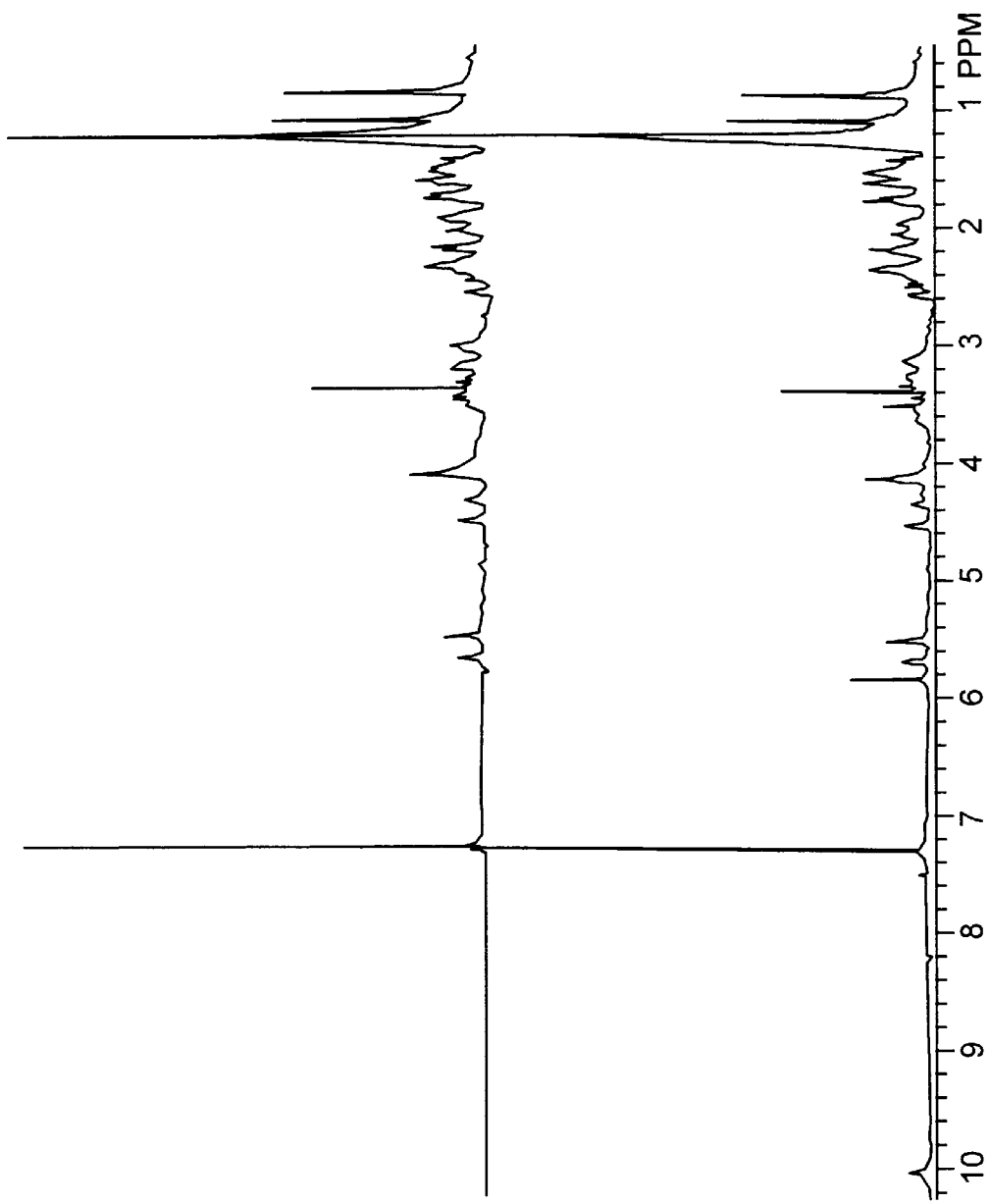
FIG. 2 shows two $^1$H NMR (CDCl$_3$, 500 MHz) spectra of Crambescidin 816 (upper plus D$_2$O).
Figure 3:
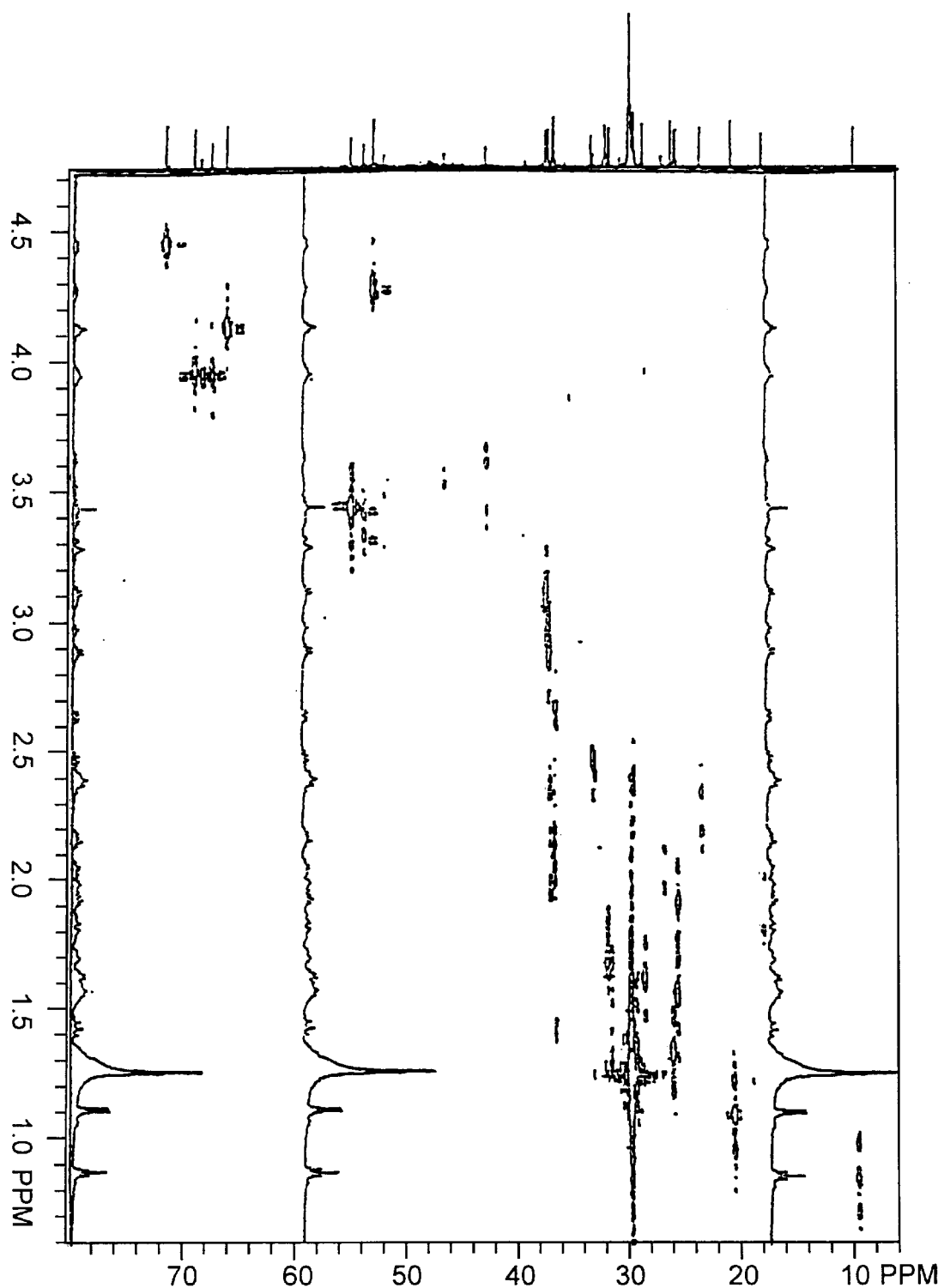
FIG. 3 is a CSCM (MeOD) spectrum of Crambescidin 816.
Figure 4A:
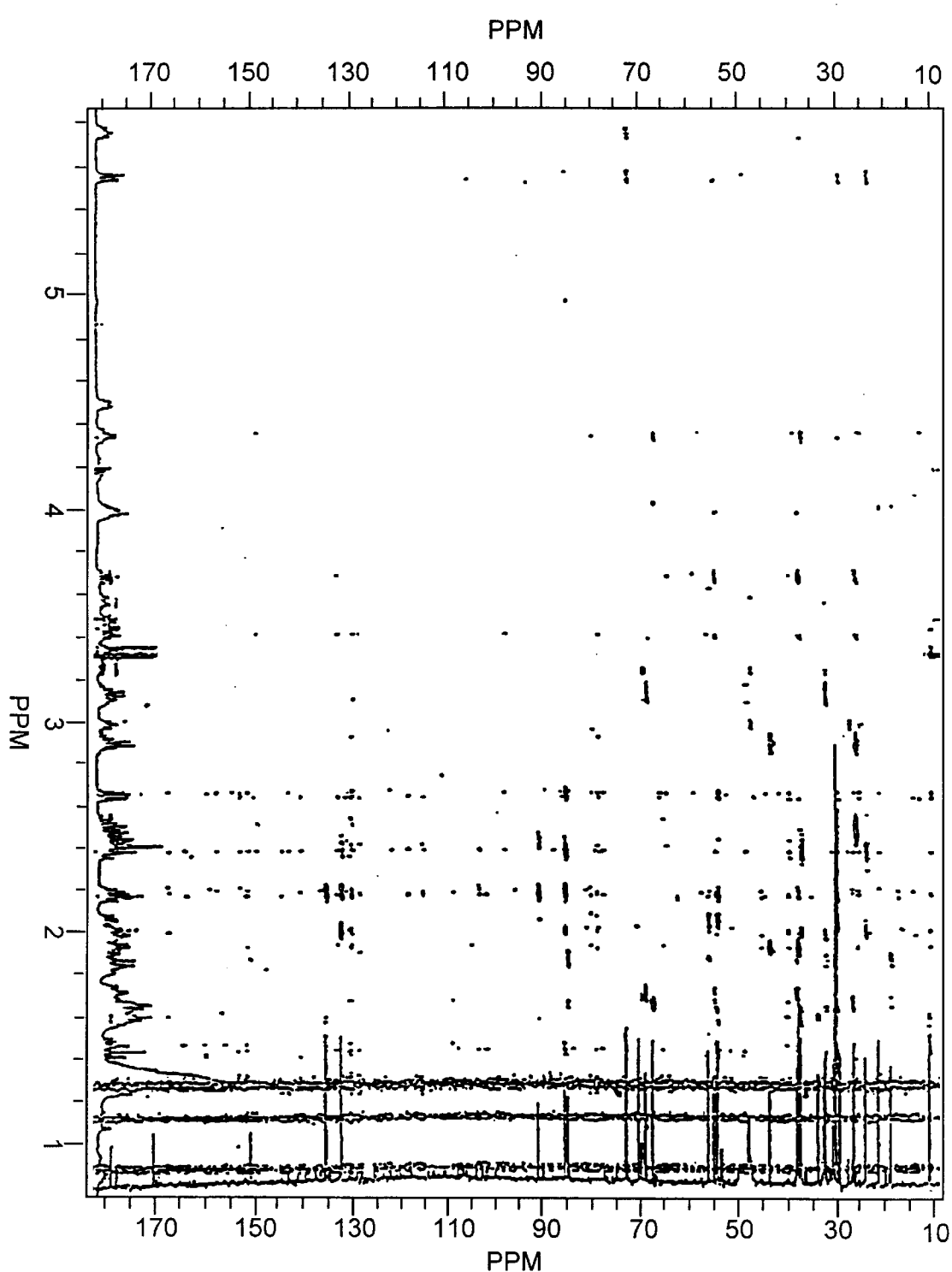
FIG. 4a is an HMBC (MeOD) spectrum of Crambescidin 816.
Figure 4B:
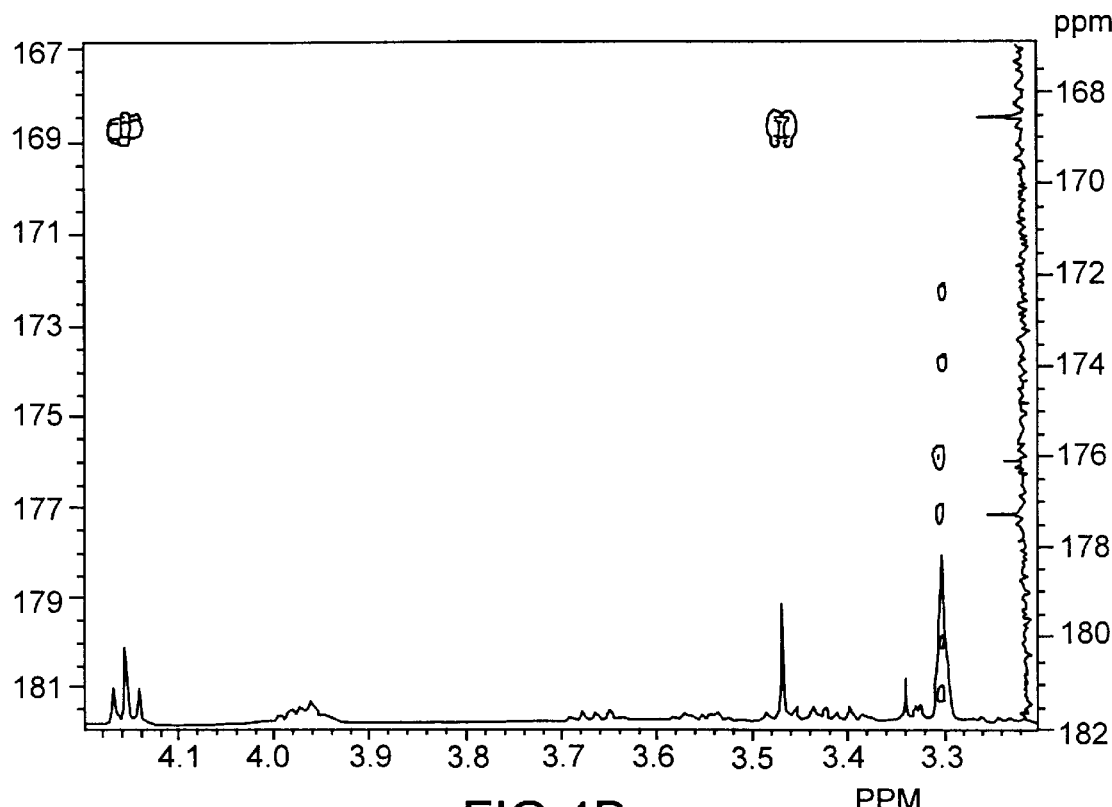
Figure 4C:
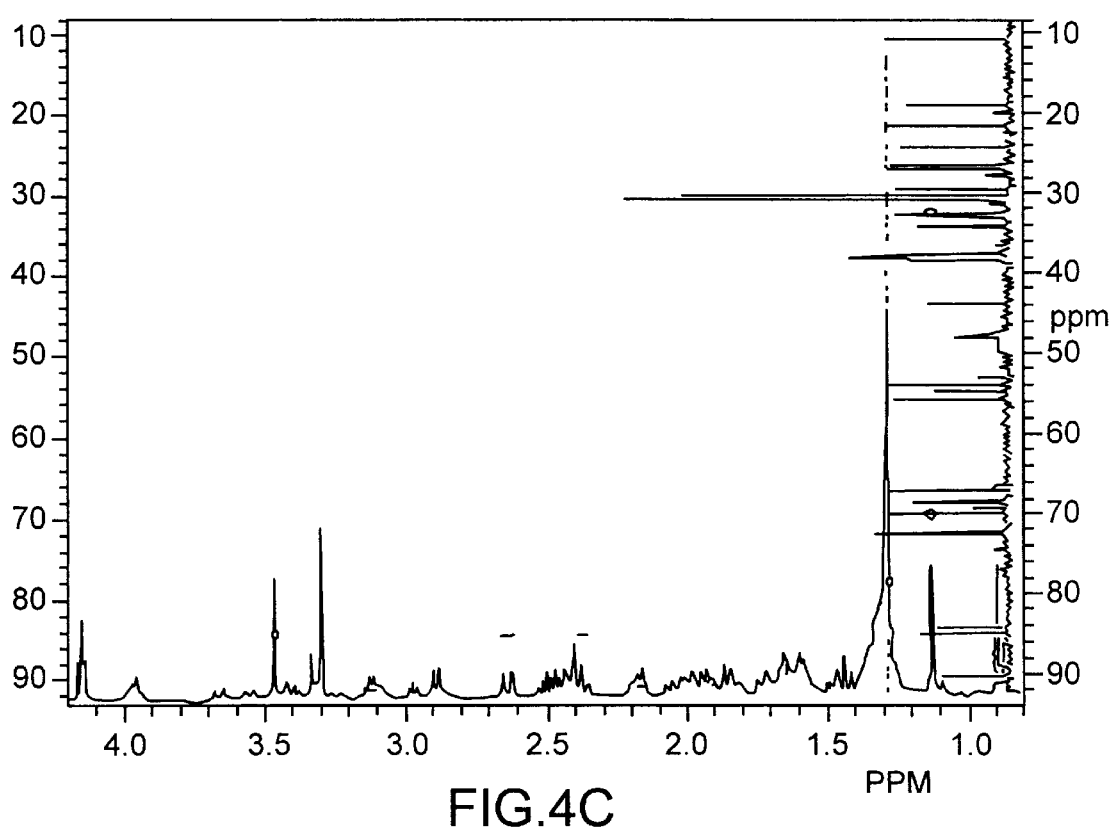
Figure 5:
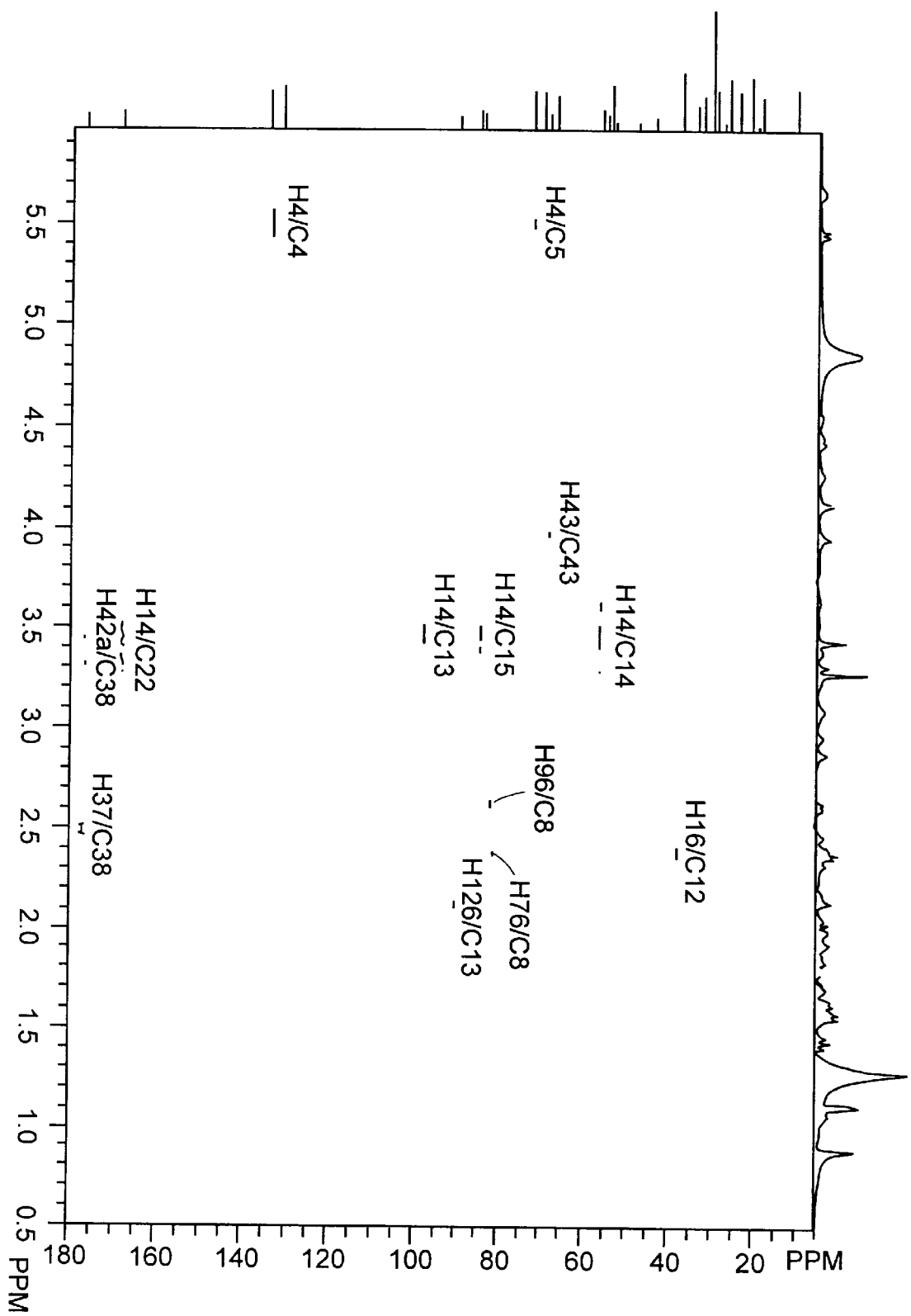
FIG. 5 is a COLOC (MeOD) spectrum of Crambescidin 816.
Figure 6:
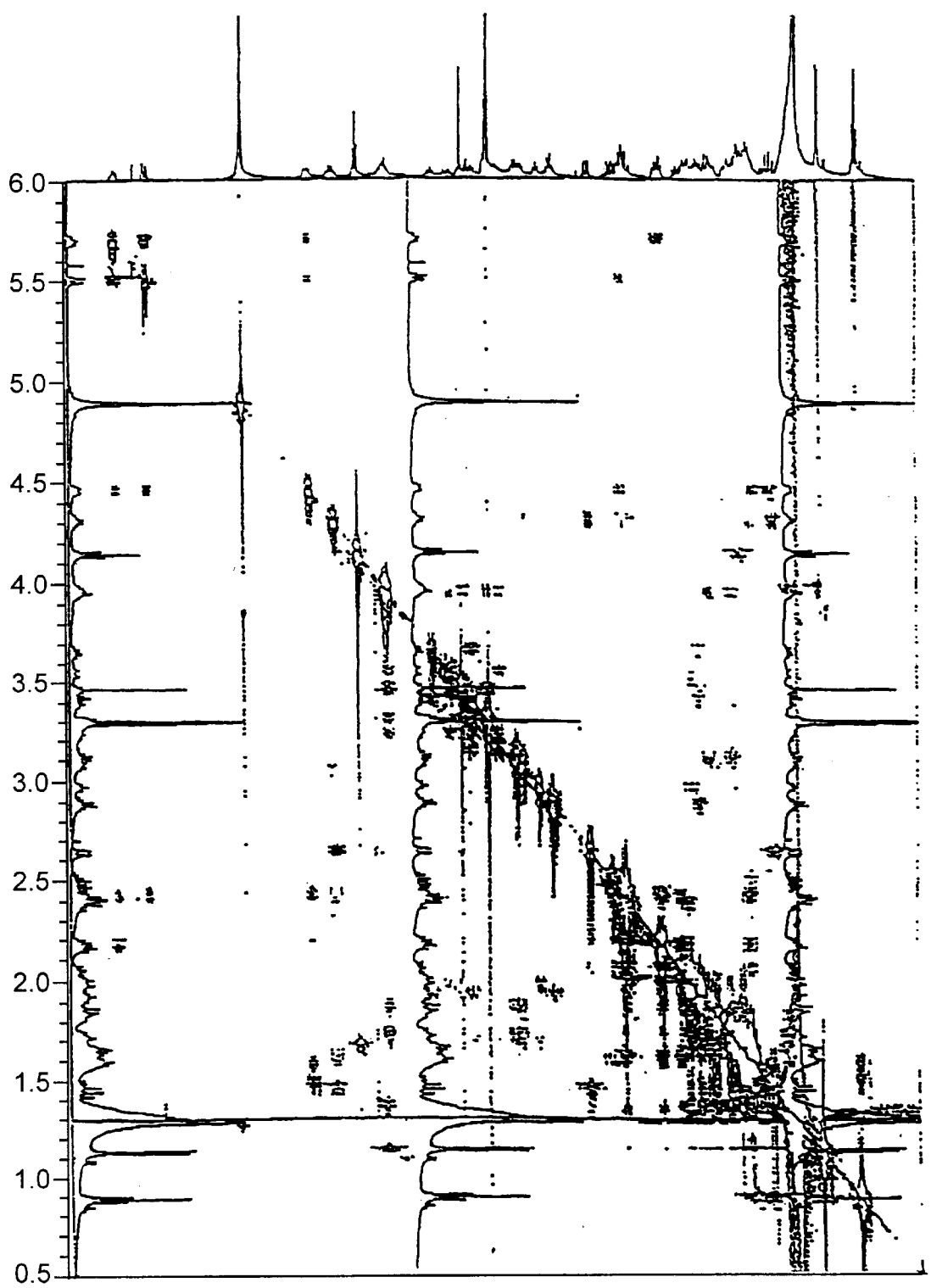
FIG. 6 is a HYPS-COSY spectrum of Crambescidin 816.

Compound 1 has the following physical/chemical properties; colorless oil; [α]$^{25}$D- −20.14 (c 0.4, MeOH); $^1$H NMR (CD$_3$OD, 500 MHz), see Table I; $^{13}$C NMR, see Table II; HRFABMS, 817.6151 (M+H), see Scheme II; FABMS, see FIG. 7; FABMS/MS, see FIG. 1; $^1$H NMR (CDCl$_3$, 500 MHZ), see FIG. 2; (D$_3$OD, 500 MHz), see Table I, $^{13}$C NMR, see Table II; COSY (MeOD, 500 MHz), see FIGS. 6a and b; HETCOR (MeOD), see FIG. 3; HMBC (MeOD), see FIG. 4; COLOC (MeOD), see FIG. 5.

Figures 1, 7:
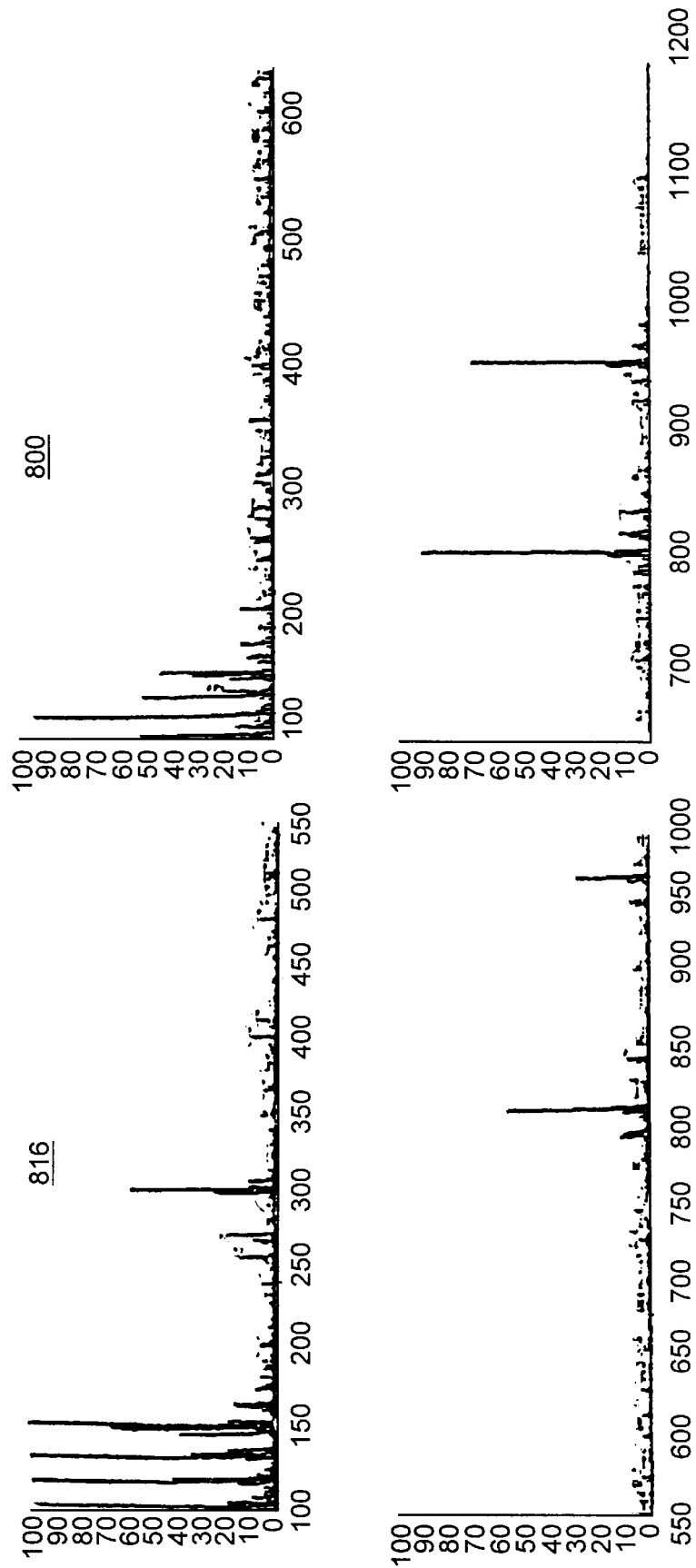
Figures 2, 7:
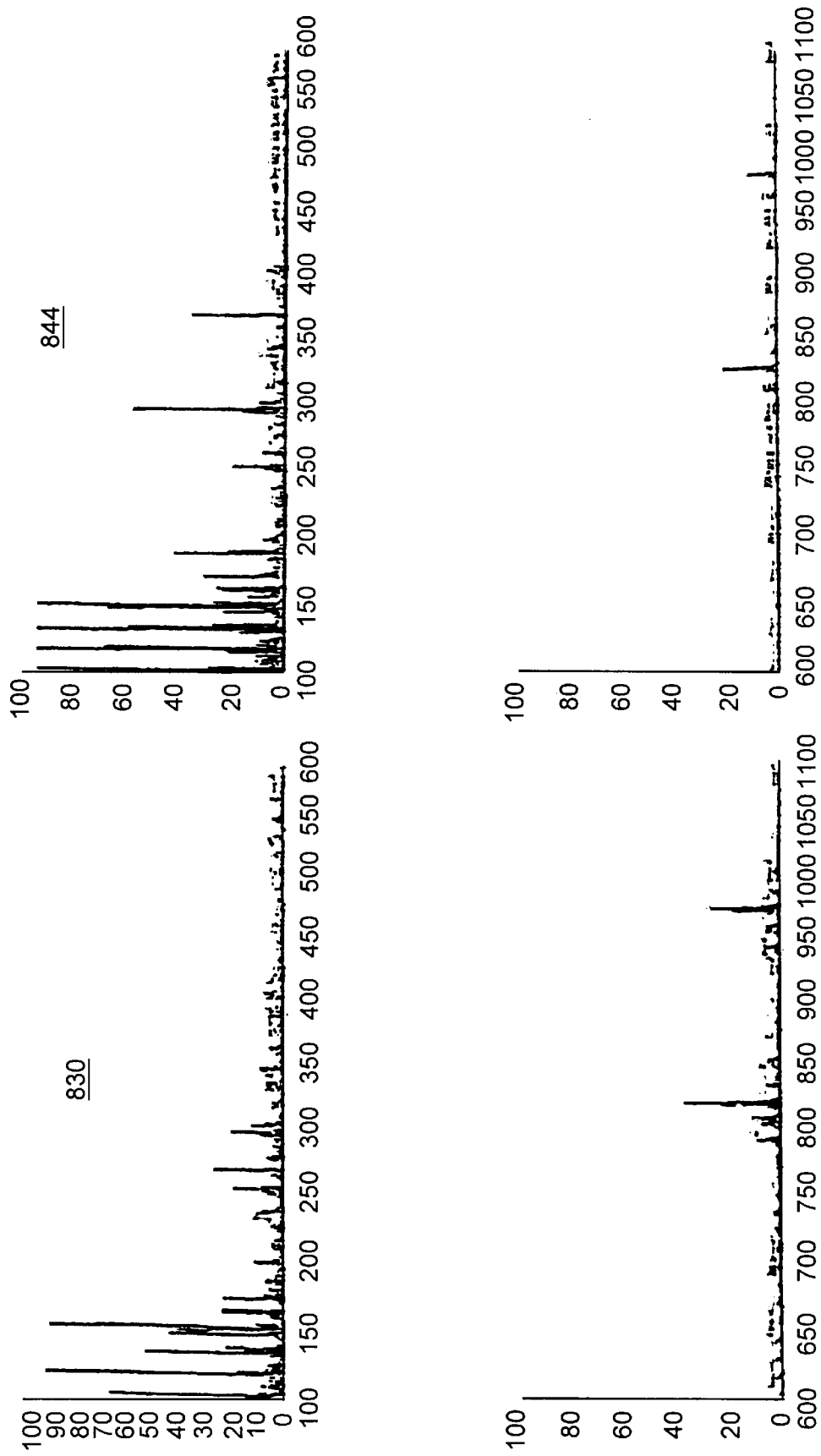
Figure 8:
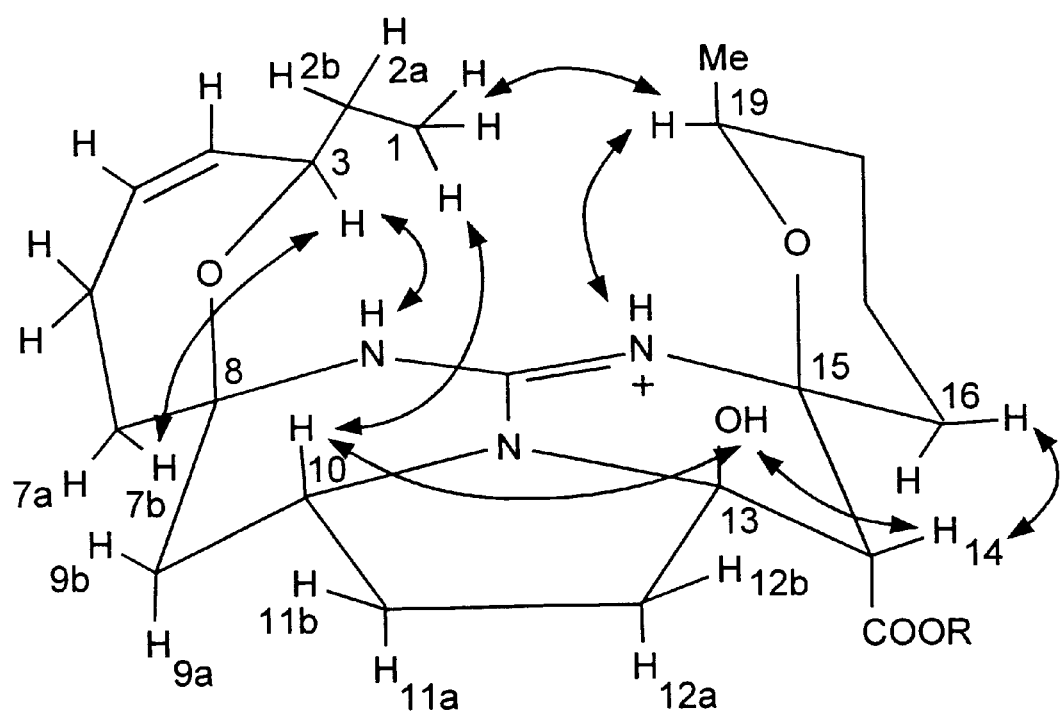
FIG. 8 shows NOE and ROESY correlations for the compounds of the present invention.
Figure 9:
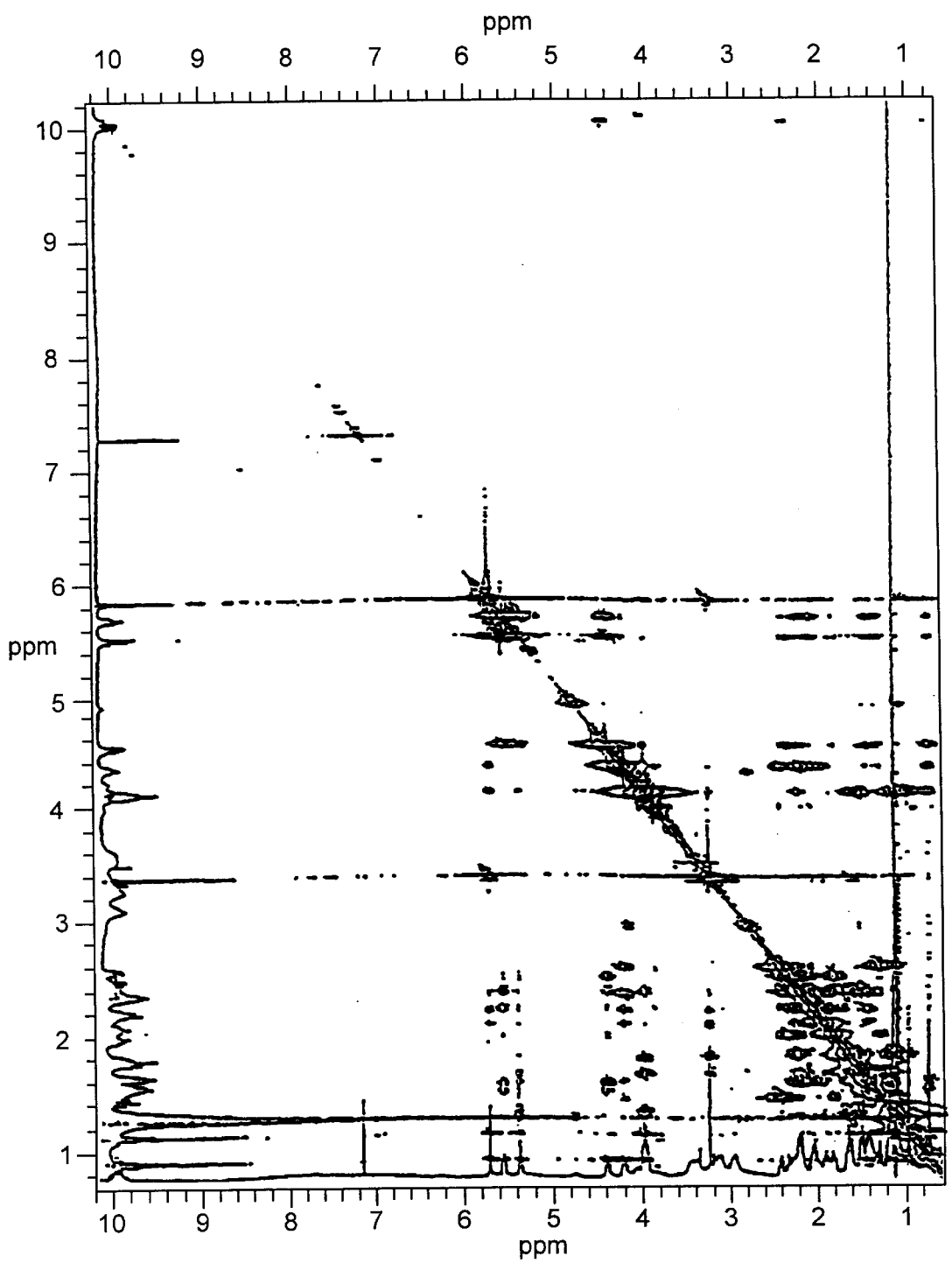
FIG. 9 is the ROESY (CDCl$_3$) spectrum of Crambescidin 816.

Crambescidin 830 (Compound 2):

Compound 2 is a colorless oil; having a HRFABMS 831.6300 (M+H); FABMS and FABMS/MS, as shown in FIGS. 7 and 1 respectively.

Crambescidin 844 (Compound 3):

Compound 3 has the following physical and chemical properties; colorless oil; [α]D$^{25}$—10.32° (c 0.19, MeOH); FABMS see FIG. 7; HRFABMS 845.6471 (Δ 0.9 mmu); FABMS/MS, see FIG. 1; $^{13}$C NMR, see Table II; $^1$H NMR (MeOD, 500 MHz) δ0.89 (t, J=7 Hz, 3H, H-1), 1.12 (d, J=6.5 Hz, 3H, H-20), 1.43 (t, J=13 Hz, 1H, H-9), 2.65 (dd, J=4.5, 13 Hz, 1H, H-9b), 2.88 (m, 2H, H-41), 3.00 (m, 2H, H-45), 3.42 (s, 1H, H-14), 3.67 (m, 1H, H-39b), 3.98 (m, 2H, H-19 and H-43), 4.18 (t, J=6.5 Hz, 2H, H-23), 4.31 (m, 1 H, H-10), 4.48 (br d, 1H, H-3), 5.51 (br d, 1H, H-4), 5.72 (br t, 1 H, H-5).

Crambescidin 800 (Compound 4):

Compound 4 has the following physical and chemical properties; colorless oil; HRFABMS, see Scheme II; FABMS and FABMS/MS, see FIGS. 7 and 1, $^{13}$C NMR, see Table II. Further purification was carried out after acetylation (Ac$_2$O/Pyridine, room temperature, overnight) by HPLC (RP (C-18 column, dp=5 μm; MeOH/0.1 M NaCl (9:1); flow rate 1.8 mL/min.; detection by RI) affording 5.9 mg of a major compound (t$_r$=16.35 min.) and some other minor compounds that are still being identified.

Example 2
Acetylation of Crambescidin 816

A solution of Crambescidin 816 (8 mg) in pyridine (1.4 mL) was stirred at room temperature overnight with excess Ac$_2$O. The resulting evaporation residue was purified by reversed-phase chromatography (RP-18) (MeOH/0.1 M NaCl) (8:2) to yield 9.1 mg of acetylated material.

The resulting compound, 43-O-Acetyl-41,45-N,N'-diacetyl-Crambescidin 816, has the following physical and chemical properties: HRFABMS 943.6497, C$_{51}$H$_{87}$N$_6$O$_{10}$ (Δ −1.3 mmu); $^1$H NMR (MeOD, 300 MHz) δ 0.89 (t, J=7 Hz, 3H, H-1), 1.13 (d, J=6.5 Hz, 3H, H-20), 1.32 (br s, H-26 to H-34), 1.42 (t, J=13 Hz, 1H, H-9a), 1.43 (m, 1H, H-2a), 1.92 (s, 3H, NCOCH$_3$), 1.94 (s, 3H, NHCOCH$_3$), 2.01 (s, 3H, OCOCH$_3$), 2.63 (dd, J=4.5, 7.3 Hz, 1H, H-9b), 3.20 (m, 4H, H-45 and H-41), 3.40 (m, 1H, H-42a), 3.48 (s, 1H, H-14), 3.58 (m, 2H, H-39 and H-42), 3.95 (m, 1H, H-19), 4.16 (t, J=6.5 Hz, 2H, H-23), 4.32 (m, 1H, H-10), 4.45 (br d, 1 H-3), 5.15 (m, 1H, H-43), 5.51 (br d, J=11 Hz, 1H, H-4), 5.71 (br t, 1H, H-5).

Example 3
Acetylation of Crambescidin 800

Example 2 was repeated using Crambescidin 800 as the starting material. The resulting compound 43-O-Acetyl-41, 45-N,N'diacetyl-crambescidin 800, has the following physical and chemical properties; HRFABMS 927.6550, C$_{51}$H$_{87}$N$_6$O$_9$ (δ −1.5 mmu); $^1$H NMR (MeOD, 300 MHz) δ 0.82 (t, J=7 Hz, 3H, H-1), 1.08 (d, J=6.5 Hz, 3H, H-20), 1.29 (br s, H-26 to H-34), 1.40 (t, J=12.7 Hz, 1H, H-9a), 1.88 (s, 3H, NHCOCH$_3$), 1.90 (s, 3H, NHCOCH$_3$), 2.01 (s, 3H, OCOCH$_3$), 2.62 (dd, J=4.5, 12.8 Hz, 1H, H-9b), 3.07 (d, J=5.6 Hz, 1 H, H-14), 3.18 (m, 4H, H-45 and 41), 3.35–3.58 (4 H, H-42 and H-39), 3.82 (m, 1H, H-19), 4.05 (m, 1H, H-13), 4.12 (t, J=6.5 Hz, 2H, H-23), 4.32 (m, 1H, H-10), 4.38 (m, 1H, H-3), 5.12 (m, 1H, H-43), 5.50 (br d, 1H, H-4), 5.70 (br t, 1H, H-5).

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of treating Herpes simplex virus type 1 infections in mammals, comprising administering to a mammal in need of such treatment, a pharmaceutical composition consisting essentially of a pharmaceutically acceptable diluent or carrier and an effective antiviral amount of the compound crambescidin 816.

2. A method of treating Herpes simplex virus type 1 infections in mammals, comprising administering to a mammal in need of such treatment, a pharmaceutical composition consisting essentially of a pharmaceutically acceptable diluent or carrier and an effective antiviral amount of the compound crambescidin 844.

3. A method of treating Herpes simplex virus type 1 infections in mammals, comprising administering to a mammal in need of such treatment, a pharmaceutical composition consisting essentially of a pharmaceutically acceptable diluent or carrier and an effective antiviral amount of the compound crambescidin 800.

* * * * *